United States Patent [19]

Mann

[11] 4,270,091

[45] May 26, 1981

[54] APPARATUS AND METHOD FOR MEASURING PRESSURES AND INDICATING LEAKS WITH OPTICAL ANALYSIS

[75] Inventor: Joseph K. Mann, Palo Alto, Calif.

[73] Assignee: Varian Associates, Inc., Palo Alto, Calif.

[21] Appl. No.: 961,806

[22] Filed: Nov. 17, 1978

Related U.S. Application Data

[62] Division of Ser. No. 872,209, Jan. 25, 1978, Pat. No. 4,147,431.

[51] Int. Cl.³ .............................................. G01L 21/32
[52] U.S. Cl. ....................................................... 324/462
[58] Field of Search ...................................... 315/111.9; 324/462–464, 470

[56] References Cited

U.S. PATENT DOCUMENTS

| | | | |
|---|---|---|---|
| 3,280,365 | 10/1966 | Young | 324/462 |
| 3,378,712 | 4/1968 | Lafferty | 324/462 |

*Primary Examiner*—Michael J. Tokar
*Attorney, Agent, or Firm*—Stanley Z. Cole; Edward H. Berkowitz

[57] ABSTRACT

A partial pressure gauge utilizes an efficient electron collision excitation source yielding de-excitation radiation characteristic of residual gases. The intensity of a given spectral line is proportional to the partial pressure of the gas having such spectral line, and the current drawn from the excitation source provides a measure of the total pressure. A calibration technique based upon comparing the emitted light intensity with the ion currents associated with the excitation process yields an accurate measure of the relative partial pressure. Use of a filter to selectively pass radiation from a known constituent in known proportion in ambient gas provides an indication of the presence of a leak without the need for probing with a test gas. Provision for passing an evaporant stream through the excitation region permits accurate monitoring of the evaporant flux from which deposition rate is determined. In combination with techniques for achieving high differential sensitivity to fluctuations in light output from a selected spectral line, a novel leak detector is achieved. In combination with an optically dispersive element a residual gas analyzer is obtained.

2 Claims, 11 Drawing Figures

APPARATUS AND METHOD FOR MEASURING PRESSURES AND INDICATING LEAKS WITH OPTICAL ANALYSIS

This work is a division of U.S. Ser. No. 872,209 filed Jan. 25, 1978 now U.S. Pat. No. 4,147,431.

FIELD OF THE INVENTION

The present invention relates to the fields of total and partial pressure measurement, deposition rate monitoring and leak indication.

BACKGROUND OF THE INVENTION

In the prior art, partial pressure sensitive devices have been employed to analyze or discriminate among various residual gases on the basis of ionic charge-to-mass ratio (q/m). Such instruments as the helium leak detector and the quadrupole mass analyzer are examples of the operative technique. Certain other prior art apparatus such as ionization gauges and sputter ion pumps are known to exhibit pressure response to certain gases with marked increase or decrease of sensitivity in relation to particular gases. This principle has been used in prior art for leak detection e.g., Varian, Model No. 975-0010, has employed this technique in combination with a nulling circuit for the detection of small differences in pressure gauge output when a probe gas (to which the gauge is particularly sensitive or insensitive) enters the leak and thereby disturbs the equilibrium distribution of gases within the system.

Partial pressure gauges including leak detectors and residual gas analyzers which respond to q/m are subject to ambiguity in interpretation. For example, $N_2$ and CO both exhibit integer molecular masses of 28 atomic mass units, He and $^2H_2$ both possess mass 4 a.m.u. Differences occuring in higher decimal places can be distinguished only by a sufficiently high resolution instrument. Such higher resolution is nearly always accompanied by a proportionate decrease in the magnitude of the signal, thereby imposing severe limits for pressure sensitivity for a device of given resolving power. Moreover, Achievement of adequate resolution from q/m analysis requires geometrical precision in fabrication and assembly of complex equipment.

The prior art also includes methods for partial pressure determination and leak detection based upon characteristic optical emission from selectively excited residual gases. Utilization of prior art apparatus for analysis of vacuum integrity requires a comparison to be made between the quiescent response of the instrument and the response of the instrument when a probe gas specific to the instrument is applied to a known or suspected leak. The presence of a small leak can only be known by the process of successfully probing for the leak. Consequently, a priori knowledge of the existence of a leak is limited by the precision with which the total pressure can be ascertained. The prior art, while providing means for detecting leaks by a systematic method, thus lacks provision for a priori indication of the presence of a leak.

Some prior art optical excitation pressure measurement apparatus teaches desirability of excitation with beams of electrons well defined in energy and direction in order to achieve selective excitation resulting in simple spectra. These limitations severely reduce the sensitivity of the apparatus. For an optical partial pressure gauge, signal strength is functionally related to the product $N = I \times \sigma_j(E) \times l$ where N is the molecular density, I is the current density of ionizing electron particles, 1 is the path × length of the electron current, and $\sigma_j(E)$ is the explicit energy dependent excitation cross section for a given quantum state of the molecule, atom, or ion represented in the molecular density. The quantity N is proportional to the pressure and $\sigma_j(E)$ is a function expressing the probability for exciting state j with electrons of energy E which is in principal known or measurable for each state. In general, for a wide variety of states from the infrared to the ultraviolet spectral region, $\sigma_j(E)$ rises rapidly to a maximum in the neighborhood of a few volts to 150 ev and thereafter decreases slowly but never vanishes. The energy dependence of the exictation probability is controlled by the potential energy of the ionizing electrons. Some prior art teaches maintaining the electron energy at a fixed narrow value close to the maximum of the excitation curves for selected states of interest. When these selected states are characterized by excitation curves peaking at relatively low electron energy, other states with excitation curves peaking at higher energies contribute minimally to the resulting spectrum.

SUMMARY OF THE INVENTION

The present invention implements discrimination among various gases by an analysis of the wavelength of photon emission from excited molecules, atoms or ions thereof. The relative variation in magnitude of the partial pressure fractions are obtained from the intensity variation of a selected emission line. The spectral distribution from a commonly excited sample contains the relative partial pressure information applicable to all residual gases.

If it is desired to monitor the partial pressure of only one specific gas, a filter selectively transmissive to the identifying spectral line of such gas is interposed between the excitation source (such as a Penning cell) and a light detecting device such as a photomultiplier tube. Plural gases can be monitored simultaneously by the use of plural filters of different transmission and a separate detector for each filter. Alternatively, plural gases can be monitored sequentially by plural filters selectively insertable between the excitation source and a single detector. Sequential monitoring can also be accomplished by placing a light dispersive element such as a prism or grating between the source and a detector (such as in a monochromator) adapted to sequentially view each desired area of the total spectrum provided by the dispersive element. For quantitative operation it is essential to either type of instrument (fixed spectral line or spectral distribution) to perform a calibration in order to relate light intensity measurements to partial pressures. The relationship is accomplished in the instant invention by measuring the ion current concomitant with the excitation process from which the spectral light is evolved. The signal so derived, available concurrently with the partial pressure signal and causally correlated therewith, affords additional information in operation to provide accurate calibrations of partial pressure.

The preferred excitation source is a form of ionization gauge or Penning cell designed to optimize light output. Thus a reliable relationship of ion current to total pressure is available, and the response of the light sensing element may be calibrated with respect to ion current (total pressure) to establish the partial pressure calibration for a selected gas. Because the total pressure and partial pressure measurements are causally correlated, fluctuations in total pressure proportional output are reflected in proportionate fluctuations in light output resulting in a ratio which is stable with respect to pressure fluctuations and noise in the exciter.

Light emission from the exciter can be brought out of the vacuum by a hermetically sealed window, or the photomultiplier and filter or dispersing element can be located within the vacuum.

The availability of partial pressure and causally correlated total pressure information permits an accurate, stable determination of the relative or fractional partial pressure of a particular gas. Knowledge of this parameter permits a strong inference to be drawn as to the presence or absence of a leak prior to executing a systematic search for leaks. A closed system free of leaks is typically characterized by a stable small nitrogen concentration (typically about 10%) originating from outgassing of vacuum chamber walls. A leak in proximity to a liquid nitrogen cold trap may cause the $N_2$ signal to reach substantially 100%. Atmospheric leaks are characteristic of atmospheric concentration of 78% $N_2$. Other ambient gases commonly found around vacuum systems might include for example $H_2O$ and $CO_2$ which can arise from cooling lines around or within the vacuum system, or $SF_6$ which is often employed for its excellent dielectric properties in high voltage environments. Substantial leaks of the aforementioned gases or any gas other than $N_2$ will have the effect of reducing the fractional concentration of $N_2$ from the expected value.

Particular utility is obtained when the filter pass band is located at about 3915 angstroms corresponding to a transition in the molecular nitrogen ion, $N_2^+$. Use of such a filter permits the apparatus to be used as a constant a priori indicator of leaks by noting that the expected nitrogen partial pressure of the system without a leak has either increased (nitrogen leak) or decreased (non-nitrogen leak). In addition, such an arrangement is effective as a conventional leak or locator. Leak location can be accomplished by a probing with nitrogen, (nitrogen signal increases), or with a gas other than nitrogen (nitrogen signal decreases). Increased sensitivity is obtained when light from the non-nitrogen probe gas is also detected by use of a filter selective to such gas. In this mode the combined decrease in nitrogen signal and increase in probe gas signal provides greater sensitivity. Obviously, instead of probing the outside of a container with a jet of nitrogen or non-nitrogen gas, the invention can be used to sniff the outside of a container which contains nitrogen or non-nitrogen gas. Although nitrogen is preferred as the main gas to be monitored because of its high percentage in air, other gases in air can be selected, or special gases which might be present in special environments in which the vacuum system is operating can be selected as the main gas to be monitored.

Maximum differential sensitivity is achieved by employing a null technique which provides singular advantages in the present invention as compared to nulling as previously applied to conventional total pressure gauges. A nulled total pressure gauge leak detector functions with a probe gas to which the particular gauge exhibits unusually large sensitivity or insensitivity. For example, a standard triode ionization gauge is known to exhibit a response for helium which is about 14% of the response for air at equal pressure. Thus, when a leak is blanketed by helium and helium therefore replaces air in the system, the signal from such a gauge could ultimately fall by 86%. In order to increase the sensitivity of the gauge to helium, the total signal may be nulled and additional electronic gain may be added. Probing leaks with a combination of helium and a nulled ionization gauge therefore requires a null signal which is equal to the total pressure to which the leak and evolved residual gases both contribute. Therefore, a small leak requires a null signal which is much larger than the leak proportional component. Where the residual gases are solely due to the leak (an extreme case where evolved gases represent a negligible contribution), the nulled signal is at best about 6 times the resulting probeable signal representative of the leak (86% compared to 14%.) A limit is therefore imposed, attributable to the magnitude of the noise concomitant to the large total pressure signal. A similar technique utilizing a partial pressure gauge of this invention permits a null signal to be applied which is only equal to the partial pressure signal and therefore introduces minimum noise.

A further advantage in a nulled optical partial pressure gauge leak detector of the present invention is apparent upon consideration of the effect of evolving gases upon nulled total pressure apparatus. In a leak proof system, the pressure is dependent upon outgassing from the interior surfaces of the vacuum chamber as well as the pumping speed of the evacuation pump resulting in a slow exponential time dependence of the pressure. Thus a total pressure nulling device will require frequent readjustment of the magnitude of the bucking signal to reestablish the null condition. The present invention operated with nulling will not require such frequent readjustment because the signal which is nulled is that due to the leaking gas constituent and does not change with time.

The present invention recognizes that the ultimate limit to operational sensitivity is the signal-to-noise ratio and that this sensitivity is maximized by maximizing the excitation probability of all energetically accessible states. The circulating current in a space charge limited device, such as a Penning cell, is well known to increase with the 3/2 power of the applied voltage. The rate of excitation is proportional to the number of excitation producing electrons encountered per unit time. The latter quantity which increases with the 3/2 power of the voltage will therefore overwhelm the slowly decreasing intrinsic excitation probability at energies beyond the peak of the excitation curve selected by the prior art for operation. Thus operation at high voltages is seen to enhance, rather than degrade the excitation probability per atom (or molecule). Moreover, the present apparatus sums over accessible states and integrates over the energy of all available electrons with consequent enhancement in exciting any given state.

The method and apparatus of the present invention is capable of leak detection in either a gas specific or non-specific mode of operation. The two modes, practiced together, are capable of a combined effect exceeding the individual performance of either mode considered separately. Thus the application of a probe gas to a leak simultaneously effects a probe gas-specific partial pressure gauge and a probe gas non-specific partial pressure gauge. The former gauge detects a proportional increase in partial pressure of the probe gas. The latter gauge detects a decrease in the partial pressure of an ambient gas. The resulting ratio may be employed as the basis for leak detection over a wider dynamic range than a single partial pressure gauge operating in either mode.

Accordingly it is an object of this invention to provide improved measurement of partial pressures by means of optical detection.

It is a further object to accurately relate partial pressure fluctuations with total pressure fluctuations derived concurrently and correlated therewith.

It is an object of this invention to measure and locate leaks in vacuum and pressure vessels using a spectral emission principle and a balancing circuit to achieve very high differential sensitivity.

It is again an object of the present invention to provide a device and method for a priori indication of a leak in a vacuum system.

It is a further object to provide for a priori leak indicating, and also for leak detection which permits a wide choice of probe gas.

It is yet a further object to provide leak detecting responsive either to a specific probe gas whose partial pressure is detected or to any other probe gas.

It is again an object to provide apparatus and method for leak detection which is operably responsive over a wider dynamic range of leak rate by detecting the partial pressure of both a probe gas and another gas.

It is yet again another object to provide an improved method and apparatus for monitoring a flux of a selected evaporant in film coating equipment.

DETAILED DESCRIPTION OF THE INVENTION

Figure 1:
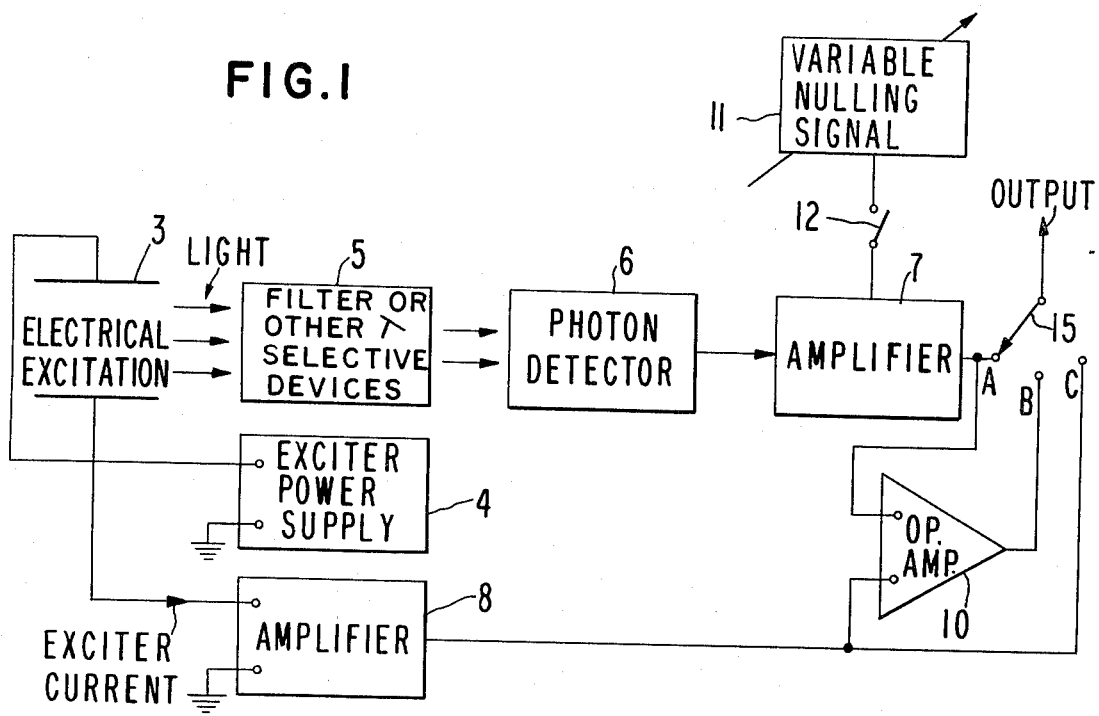
FIG. 1 is a block diagram of the apparatus of a preferred embodiment of the invention.

A general schematic illustration of a preferred apparatus appears in FIG. 1. Electrical excitation of gases and vapors is accomplished by a suitable exciter 3, as for example, a Penning cell as further described below, or a triode ionization gauge structure generally similar to that described in U.S. Pat. No. 3,267,326, or other devices of similar character e.g., a diode discharge or an electrodeless discharge. The excitation is maintained by an exciter power supply 4. Electromagnetic radiation derived from the de-excitation of atomic, molecular and ionic systems impinges a filter or other wavelength selective device 5, and the intensity of such selected radiation is sensed by an appropriate detector 6. The detector develops a signal of magnitude proportional to the intensity of the radiation within the passband of the wavelength selector and this response is directed to an amplifier 7, and is then available for output to an indicating device. When the location and width of the passband are selected to include substantially only a prominent emission line or lines characteristic of a particular gas or vapor, the resulting signal is proportional to the partial pressure thereof. The exciter current, non-selectively proportional to the local numeric density of all atomic and molecular systems, is also directed to an amplifier 8 and made available for output from which a total pressure may be ascertained. An operational amplifier 10 independently forms the difference of the wavelength selected signal and the exciter current signal. This combined signal is also available for output. The respective amplifiers 7 and 8 are most conveniently logarithmic in response in which case the operational amplifier output is proportional to the logarithm of the ratio of the two signals. If the respective amplifiers are linear in response a simple difference is available at the output of the operational amplifier. Finally a variable nulling signal 11 is available through a switch 12, if it is desired to bias the wavelength selected signal. In use, this apparatus can provide a variety of outputs depending upon the selected setting of three-way switch 15. More specifically, if switch 15 is set on contact A, the output is proportional to partial pressure of a specific gas. Contact C gives an output proportional to total pressure of all gases. Contact B gives the logarithm of the fractional partial pressure relative to the total pressure or the difference if linear amplifiers are used. The nulling feature allows increased amplifier gain to be used so as to detect very small changes in signal strength.

Figure 2:
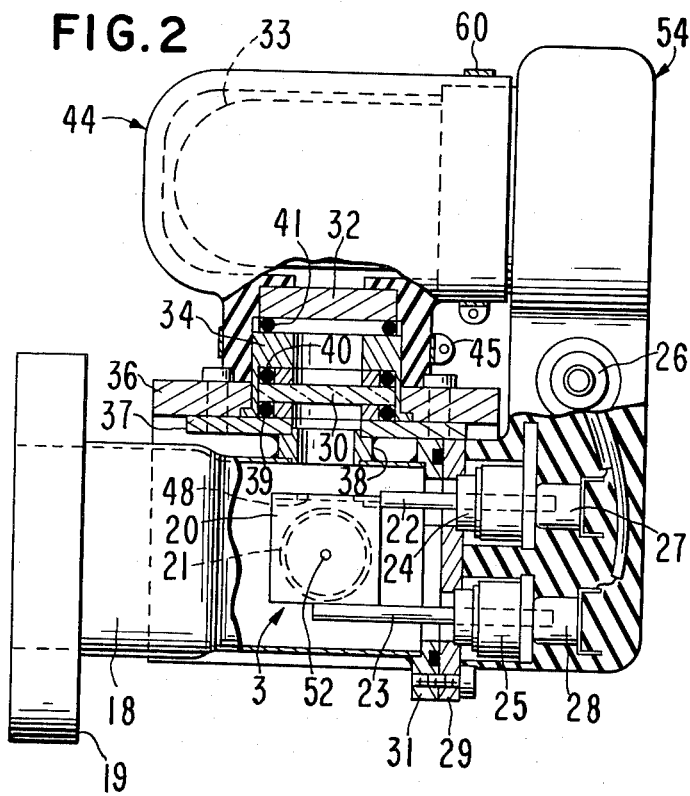
FIG. 2 is a partial cross section of a preferred embodiment.

FIG. 2 illustrates a specific preferred embodiment of the invention. A cylindrical metal housing 18 is adapted for hermitic sealing to a test vacuum system, not shown, by flange 19. The specific form of exciter 3 comprises a U-shaped cathode 20 (see also FIG. 4) and cylindrical metal anode 21, which are supported within the housing by respective conductors 22 and 23, and respective insulated hermetically-sealed feed-throughs 24 and 25. Feed-throughs 24 and 25 are brazed in an end plate 29. An end flange 31 is brazed to housing 18, and plate 29 is bolted to flange 31 with an interposed sealing ring forming a hermetic seal. Electrical leads from conductors 22 and 23 are taken to high voltage leads of a multi conductor cable 26 via metal sockets 27 and 28. A magnetic field is maintained perpendicular to the plane of FIG. 2 within the confines of the region of the Penning cell defined by the cathode-anode combination by a magnet structure described below. Light evolved within the Penning cell exits the housing through a window 30 of glass or other light transmitting material, and a selected wavelength interval is transmitted by a filter 31 thence falling upon a conventional photomultiplier 33. For access and replacement, window 30 is removeably mounted within an annular metal alignment tube 34 which is held in place by a magnetic yoke 36 bolted to a metal flange 37 which is brazed to metal stand-off collar 38 which is in turn brazed to housing 18 in alignment with a light-transmitting aperture in the housing. Window 30 is hermetically sealed to flange 37 of the housing by a gasket 39. Gaskets 40 and 41 are provided to protect window 30 and filter 32 respectively from mechanical stresses and to prevent external light from reaching detector 33. A light tight housing 44 formed of molded rubber and containing the optical filter is clamped to alignment member 34 by a hose clamp 45.

Figure 3:
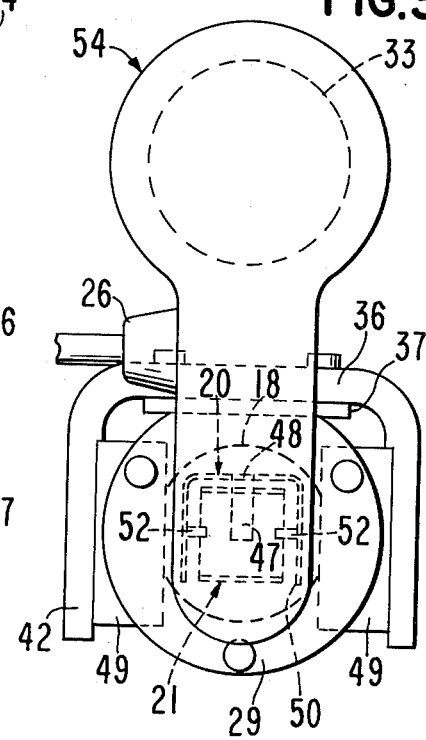
FIG. 3 is a view of a view of the apparatus from the right of FIG. 2.
Figure 4:
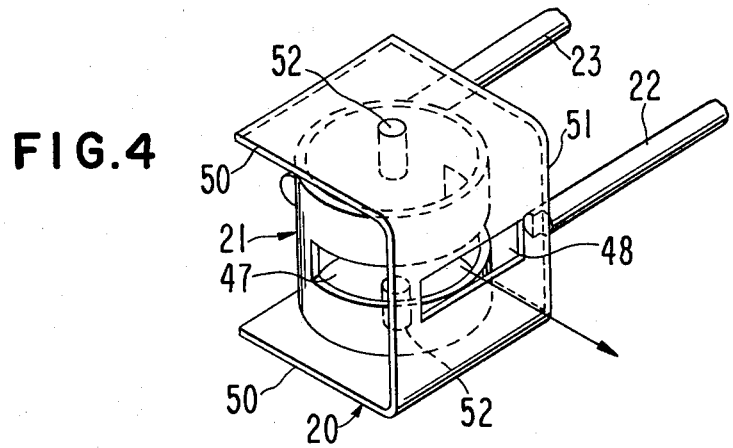
FIG. 4 is a perspective view of the exciter of FIGS. 2 and 3.

Referring additionally to FIGS. 3 and 4, the relationship of cathode 20 and anode 21 is apparent. Anode 21 is a stainless steel tube, typically 0.60 inches I.D. by 0.60 inches in length. Approximately the center ⅓ of the tube is removed over substantially one-half of its circumference to form a slot 47 for light output. Cathode 20, is formed of sheet material typically 0.050 inch × 0.80 inch × 2.4 inch formed into a U-shaped member approximately 0.8×0.8 square. The cathode is preferably made of non-active metal such as stainless steel to minimize pumping and outgassing by the Penning cell exciter. It will be apparent to one skilled in the art that the cathode can be made of active metal so that the cathode-anode-magnet arrangement serves also as the pump for the system. When fractional partial pressure is being measured, pumping speed variations will not appreciably effect the fractional pressure reading and thus will not appreciably effect leak indication or leak detection. The parallel end faces of the U-shaped cathode baffle the open ends of the cylindrical anode, and a window 48, cut from the middle face of the cathode, is aligned with the slot 47 in anode 21. A magnetic field of approximately 1000 gauss is applid along the axis of the anode between a pair of permanent magnets 49 attached to magnetic yoke 36. The yoke 36 completes the magnetic circuit between magnets 49. The center portion of the U-shaped yoke is apertured to fit around the alignment tube 34. Thus when the center portion of yoke 36 is bolted to flange 37 it serves the multiple function of locating the magnets in proper position and also securing the alignment tube 34 and window 30 to the housing 18. Interposing the yoke between the photomultiplier and the exciter has the beneficial effect of minimizing stray magnetic field in the neighborhood of the photomultiplier. In operation, a negative electrical potential of −2 KV with respect to ground is impressed on the cathode, creating an electric field between the cathode and the anode which is at ground potential.

Referring again to FIG. 4, there is shown a perspective view of the exciter of FIGS. 2 and 3 but oriented differently for better viewing. The exciter is a Penning cell so designed as to optimize transmission of the light evolved therein. The middle section of the U-shaped cathode 20 is interposed between the slotted anode 21 and the photosensor in order to protect optical transmission surfaces from degradation which could conceivably arise upon lengthy operation. More specifically, sputtering of cathode material from parallel plate portions 50 of the cathode is effectively baffled from the direct view of the window 30 by the unapertured central portion 51 of the cathode structure. An equally effective approach is realized if independent baffles (not shown) are interposed between the window and anode slot to preclude direct incidence of sputtered material from cathode surfaces on the window. If this approach is used, the U-shaped cathode may be oriented advantageously with the middle section thereof rotated 180 degrees about the axis of cylindrical anode 21 from the position shown, and the middle section can be solid. Projections 52 are a feature of Penning cell design well known in the art which facilitate the initiation of the discharge. Projections 52 can be a single rod extending completely between cathode plates 50 to provide full magnetron type operation.

Figure 10:
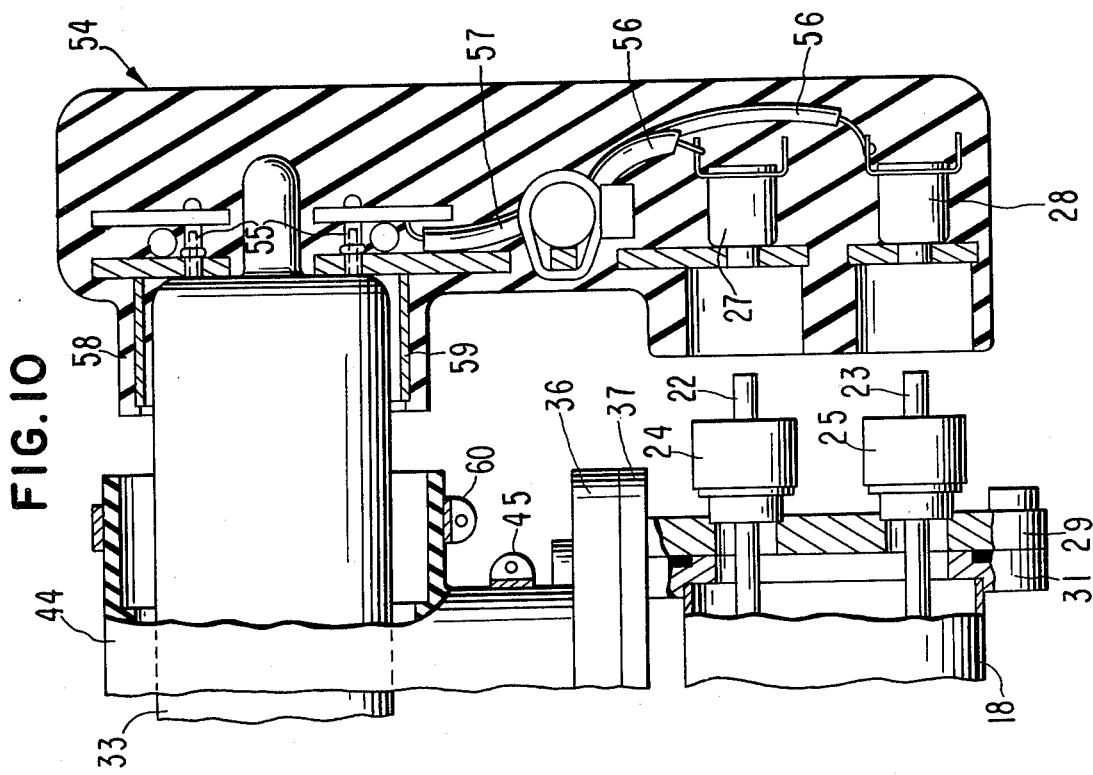
FIG. 10 is an exploded view of a portion of FIG. 2.

Referring now to FIG. 10 in relation to FIGS. 2 and 3, the details of the structure for holding sockets 27 and 28 will be described. The structure comprises a one-piece molded rubber socket unit 54. The socket unit is molded around the sockets 27 and 28 which receive the Penning cell conductor rods 22 and 23, and is also molded around a twelve spin socket recepticle for the photomultiplier tube 33. Two of the twelve pin sockets are shown at 55. Also molded in the socket unit is the multi-wire cale 26 having leads 56 for the Penning cell and the necessary leads (one being shown at 57) for the photomultipler socket 55. FIG. 10 is an exploded view of a portion of FIG. 2 to assist in describing the procedure for assembling the structure of FIG. 2. First the rubber housing 44 containing the optical filter is positioned over alignment tube 34 and held in physical and light-tight position by clamp 45. Then the one-piece socket unit 54, with photomultiplier tube pins inserted in sockets 55, is pressed against end plate 29 to receive the Penning cell conductors 22 and 23 in sockets 27 and 28. At the same time, the photomultiplier tube 33 enters the molded rubber housing 44, and the right end of housing 44 slides over an annular projection 58 of the socket unit. Projection 58 is lined with a reinforcing tube 59. Finally, the socket unit is held in place by a hose clamp 60.

Figure 5:
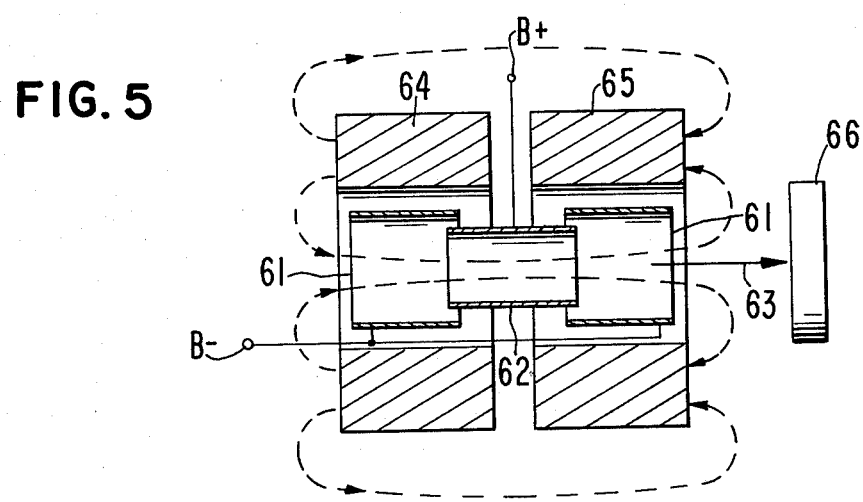
FIG. 5 shows a schematic view of another form of exciter.

Referring now to FIG. 5 another embodiment of a Penning cell type exciter is shown. Two cylindrical electrodes 61 are spaced apart on a common axis to form cathodes. A cylindrical anode 62 of smaller or larger radius is coaxially disposed intermediate the cathodes. The magnetic field (shown by dashed arrow lines) is applied parallel to the axis as for example by annular permanent magnets 64 and 65, and light output available along this axis is indicated by arrow 63. It has been found that the window 66 so situated for this manner of light derivation is less likely to become subject to degradation in optical transmission characteristics caused by a coation of particles sputtered off the cathode surfaces by bombardment with ions from the glow discharge in the Penning c ell. It is believed that direct ion bombardment serves to remove deposits of contaminants which might otherwise gradually accumulate on window 66. When the window is thus cleaned it will charge to a positive voltage and repel ions which could otherwise sputter-etch the window giving a cleaning but self-limiting, effect.

Figure 6:
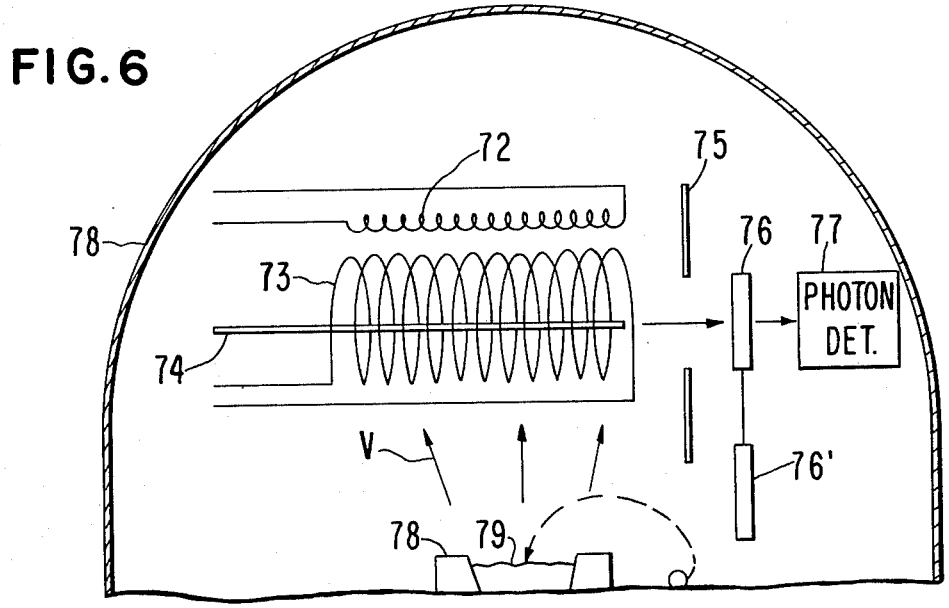
FIG. 6 shows a schematic view of another embodiment of the invention employing yet another type of exciter.

Now referring to FIG. 6, there is illustrated an exciter of the type well known in the art as a triode ionization gauge such as shown in U.S. Pat. No. 3,267,326. An electron emitting filament 72 provides a source of electrons which acquire energy in accelerating toward a highly transparent gridded anode structure 73 maintained at a positive potential with respect to the filament. Typically the filament is at approximately +45 volts and the grid at approximately +180 volts. Ions produced by electrons colliding with gas particles within the volume defined by the anode are collected by a central collector electrode 74 which is maintained at a potential negative with respect to both the anode and filament, as for example at ground potential. The ion current derived from the collector is proportional to the total pressure as is well known in the art. The anode defines a potential well from which electrons cannot escape save by interception by the anode structure (additional grid wires across the ends of the cage are not shown). Consequently, the typical electron traverses this region many times. A portion of the de-excitation light is transmitted by a filter 76 and falls upon a photon detector 77. Stray light evolved by the filament 72 is effectively baffled by an annular paerture plate 75. This figure also illustrates two additional featues which are not peculiar to the illustrated form of exciter. First the apparatus is shown entirely within a vacuum vessel 78. This manner of placement eliminates the requirement for a window and the attenuation of the signal due to transmission through a window. Such attenuation is present at all wavelengths, but is especially severe to ultraviolet emission.

Secondly, FIG. 6 shows an arrangement in which the exciter and detector apparatus can be used to monitor deposition rates, instead of, or in additon to, measuring gas pressures. In the field of coating films onto substrates, as by vapor or cathode sputter techniques, it is important to know the rate at which the coating material is passing from the source to the substrate. FIG. 6 shows a conventional vaporization source of coating material, comprising a crucible 78 containing a material 79 subject to evaporation by heating, such evaporation being accomplished by electron impact from an electron source 80. In this embodiment, a portion of the evaporant which evolves (as shown by arrows V) is allowed to transverse the exciter, undergoing excitation and yielding characteristic spectral emission lines selected by filter 76 for detection. The signal derived therefom is proportional to the density of evaporant in the exciter region. The instantaneous rate of deposition of the evaporant upon surfaces to be coated (not shown) and the time integral thereof may therefore be known. Filter 76 is selected to pass the characteristic spectral emission lines of the material being deposited, such as the line of the material 79 in crucible 78 in the vaporization embodiment of FIG. 6. Suitable excitation means for monitoring evaporants by characteristic optical emissions thereof is not limited to ionization gauge type exciter of FIG. 6, and other exciters discussed herein may alternatively serve to optically excite an evaporant. If it is desired to use the exciter and detector of FIG. 6 for gas pressure measurement in accordance with the invention (as during start up), filter 76 can be attached to a filter 76' for passing light from the selected gas, and filters 76 and 76' can be moved upwardly to locate filter 76' in the position shown for filter 76. The movement is simply reversed to revert to depositon rate monitoring.

Various exciters of similar characteristics will readily occur to one skilled in the art for providing confined electron fluxes ahd a range of electron energies for efficient optical excitation. An arrangement of electrostatic or magnetic mirrors to confine an electron flux is one such alternative.

Figure 7:
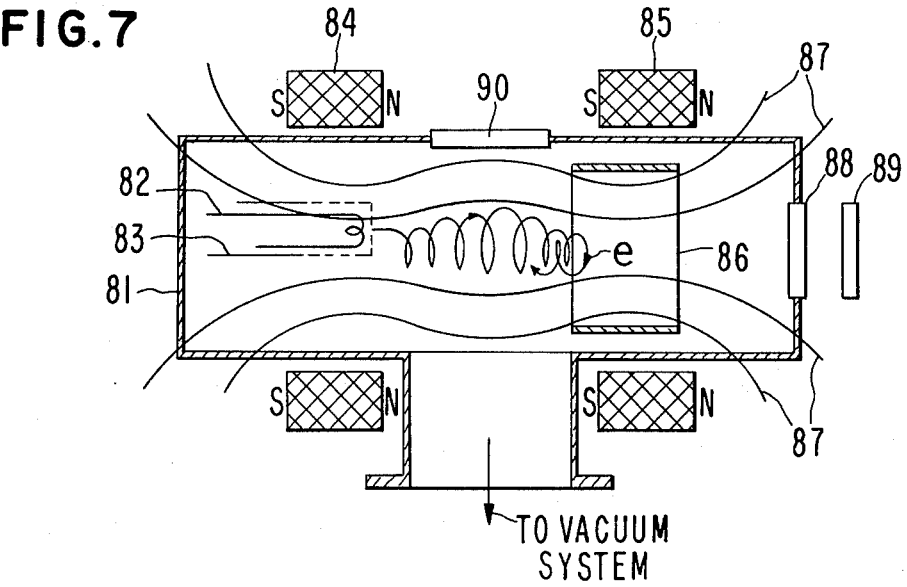
FIG. 7 shows a schematic view of a magnetic bottle exciter.

Referring now to FIG. 7 there is shown an example of the latter type apparatus, known as a magnetic mirror. The structure comprises a non-magnetic housing 81 adapted for attachment to a vacuum system. A cathode such as filament 82 injects electrons by acceleration through a gridded anode 83 into a magnetic confinement region formed by two annular magnetic sources spaced apart on a common axis as for example solenoids 84 and 85. The confined electrons execute complex trajectories principally characterized by helical motion (indicated by line e) caused by magnetic lines of force having the shape indicated generally at 87 and these electrons are reflected from regions of more intense magnetic field.

The excitation of atoms and molecules by electrons within the confined region terminates in photon emission which is transmitted by a window 8. A wavelength selective filter 89 and detector (not shown) provide the desired partial pressure signal from light out of window 88. It will be noted that the exciter of FIG. 7 need not include an ion collector for obtaining a signal representative of total pressure. Instead, an alternate means of monitoring total pressure is indicated by another window 9 from which the total light output (without a filter) is used for sensing of the total spectrum by a photosensitive device such as a conventional photomultiplier tube (not shown). It will be apparent to one skilled in the art that an ion collector, such as cylindrical electrode 86, could be included in the structure of FIG. 7. Either total light or ion current monitoring is then available for providing a causally correlated total pressure dependent signal.

Figure 8:
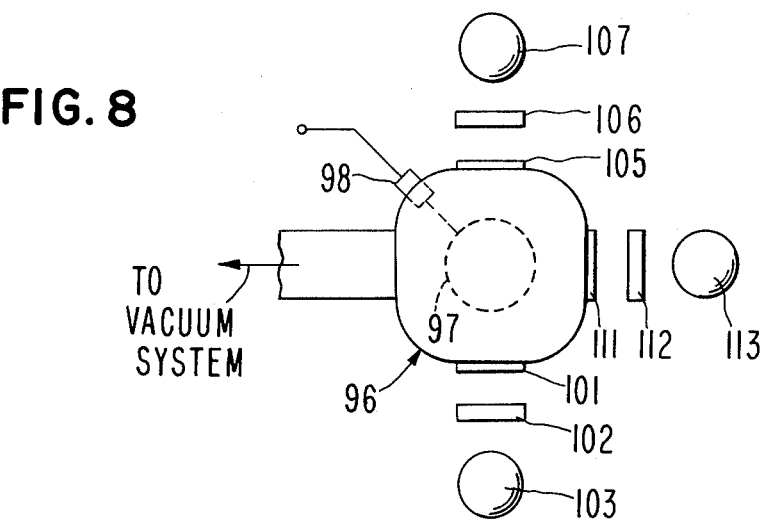
FIG. 8 shows a schematic example of a multiple gas specific partial pressure apparatus according to the present invention.

FIG. 8 illustrates three partial pressure gauges adapted to be affixed to a vacuum system. The housing 96 contains an exciter including for example a tubular gridded cage anode structure 97 as further illustrated in FIG. 9, in order to maximize light output in all directions. An external magnetic field 8 is applied along the axis of the anode. Top and bottom walls 99 of the housing 96, which walls are perpendicular to the magnetic field H, comprise the cathodes of the Penning cell thus formed. Returning again to FIG. 8, a hermetically sealed feedthrough 98 permits a potential to be established between anode 97 housing 96 and a Penning discharge may be established therein. The discharge is projected through window 101 and a filter 102 of given wavelength to a first photomultiplier 103; through window 105 and filter 106 of a different wavelength to a second photomultiplier 107, and through window 111 and filter 113 of a third wavelength to a third photomultiplier 113. In this way, three different gases can be monitored simultaneously. Obviously, the number can be increased by adding more window-filter-photomultiplier units.

The operation and interrelation of the various figures thus far disclosed will now be described in more detail. The Penning Cell exciter of FIGS. 2, 3 and 4 corresponds to item 3 of FIG. 1. The positive output exciter power supply 4 is preferably connected to anode conductor 23, and the cathode conductor 22 is connected to the input of amplifier 8. The relationship of cathode and anode conductors to power supply 4 and amplifier 8 can be interchange d if the polarity of the power supply is likewise reversed.

In the Penning cell of cylindrical symmetry shown in FIG. 5, high voltage of positive polarity from power supply 4 is applied to the terminal labeled B+ for the anode 62, and an output signal from cathodes 61 is directed to amplifier 8 via terminal B−. As with the Penning cell exciter of the previous paragraph, the relationship of cathodes and anode to power supply 4 and amplifier 8 may be interchanged together with a reversal of power supply polarity.

The ion gauge exciter of FIG. 6 is understood within the context of FIG. 1 wherein the amplifier 8 derives its input from ion current collector 74. Filament 72 is powered by an independent power supply (not shown) to achieve thermionic emission. Power supply 4 maintains the anode structure at about +180 volts with respect to the relatively negative collector 74 at ground potential in order to collect the ions formed within the region defined by the anode structure. An additional voltage source not shown maintains the filament at a positive potential with respect to the collector but less positive than the potential applied to the anode structure.

The magnetic bottle exciter of FIG. 7 utilizes power supply 4 to maintain anode 83 at a positive potential with respect to filament 82 in order to accelerate electrons therefrom for injection into the magnetic confinement region. An independent power supply (not shown) is required to supply heat to the filament 82 and a negative potential relative to anode 83 in order to maintain thermionic emission of electrons. In the illustrated version of FIG. 7 a signal representative of the total pressure is derived from the total light output. Such a signal is derived by means of an additional photo detector (not shown) which responds to the light output from window 90 without an intervening filter. The output of the aforesaid photon detector is then connected to the input of amplifier 8 of FIG. 1. Use of total light output as a representation of total pressures is probably heat confined to known compositions of residual gases. This limitation arises from the distribution of spectral lines over the wavelength interval of photodetector response. The photodetector response function is commonly a complicated empirical function of asymmetric shape. An unknown material with the greater part of its emission spectra concentrated in extreme regions of photodetector response or subject to unusually extreme (weak or strong) excitation probabilities could bring about serious discrepancy between indicated pressure and actual pressure. Where an optically dispersive element is employed and the spectrum is differentially scanned, as in a residual gas analyzer, photodetector response corrections may be automatically applied and integrated to accurately yield total pressure. If an ion collector is used in FIG. 7, it is connected to amplifier 8.

In each of these exciters the electron trajectories are confined to a local region defined by an electrostatic or magnetic constraining field. Repetitive traverses of the local region result in path lengths which are on average several times the dimensions of the confinement region. Thus in the Penning cell of FIGS. 2, 3 and 4, electrons are largely confined to the cylindrical region defined by anode 12. This is accomplished by the magnetic field aligned parallel with the axis of the cylinder which contrains the motion in the radial direction and the negative electrical potential of the cathode 20 which constrains motion at the axial extremes of the exciter resulting in a "reflection" of the trajectory. The electron trajectories will thus have the general character of helices along the axis of the magnetic field or cycloidal paths depending upon the initial position, speed and direction of the electron and the relative magnitude and orientation of the electric and magnetic fields with respect to the instantaneous electron momentum. Collisions with gas molecules will also tend to distribute the energy over the entire range from zero energy to maximum energy resulting in a lower energy electron.

Figure 9:
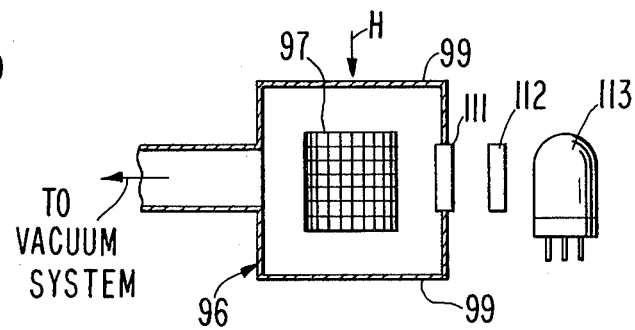
FIG. 9 is a cross section through the axis of FIG. 8.

In the embodiment of FIGS. 8 and 9, the positive output power supply 4 is connected to anode 97, and the cathode walls 99 are connected to the input of amplifier 8. As mentioned before the relationship of cathodes and anode to power supply 4 and amplifier 8 may be interchanged if the power supply output is made negative.

Figure 11:
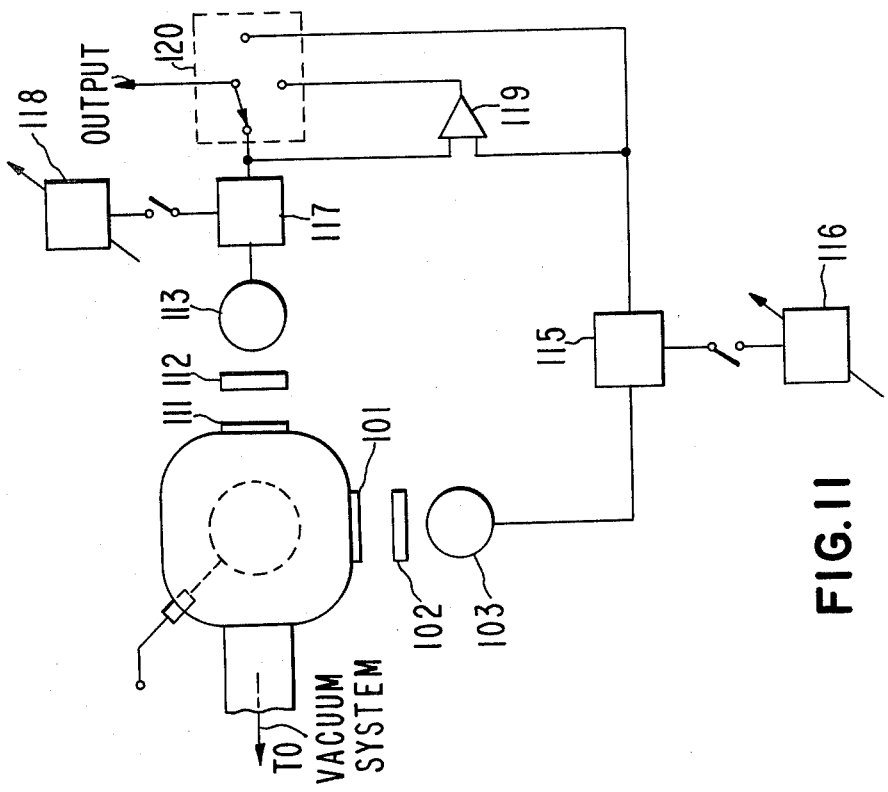
FIG. 11 shows a schematic view of an embodiment having increased sensitivity for leak detection.

In another embodiment shown in FIG. 11, the arrangement of FIGS. 8 and 9 is shown with only two optical partial pressure gauges employed in a cooperative engageament to produce a leak analysis instrument with sensitivity spanning a dynamic range characteristic of both a single channel instrument and a correlated dual channel instrument. In other words, when probing with a single gas, changes in partial pressure of that gas can be measured to give a signal representative of changes in the pressure of the probe gas alone; or changes in the partial pressure of the probe gas and changes in the partial pressure of a gas already present in the system can both be measured and correlated with each other to provide increased sensitivity. Filter 112 and detector 113 are selected to detect a spectral line characteristic of the dominant rsidual gas due to the leak, for example, $N_2$. A filter 102 and detector 103 are selected to detect a spectral line characteristic of any probe gas other than the aforesaid leaking gas selected by filter 112 and which gas is not ordinarily present in the outside environment of the leaking enclosure. $CF_4$ is an example of such a gas which is found to be strongly excited by the present method and provides a good signal. When an atmospheric leak is probed with the probe g s, the air leak rate diminishes and the dominant residual leak related signal, e.g. $N_2$, therefore decreases. Concurrently the signal for the probe gas increases. The respective partial pressure signals are processed by amplifiers 115 and 117 and are independently available for output. Variable nulling current sources 116 and 118 are available to bias the respective signals for purposes of signal enhancement, but in operation preferably only one of the nulling sources would be used at a given time. The signals are combined by operational amplifier 119 to produce the difference thereof which is proportional to the logarithmic ratio if amplifiers 115 and 117 have logarithmic response. Alternatively the linear difference is formed by operational amplifier 119, if amplifiers 115 and 18 have linear response. The logarithmic ratio of the two partial pressures, causally correlated by the leak rate, provides a highly sensitive response for leak location and measurement and is preferred therefore. The partial pressure signals may be balanced against one aother by means well known in the art to yield a signal out of amplifier 119 defining a quiescent state with increased sensitivity. The departure from the quiescent condition indicates that a leak has been covered by the probe gas. When signal strength is sufficient for the purpose, either detection channel may be independently selected, as by switch 120, for output indication. Such single channel response may be upward-reading or downward-reading depending upon whether the probe gas detection channel or residual gas detection channel is selected. The selection of gases and of particular spectral lines for detection provides an additional freedom to tailor the sensitivity of the apparatus to particular combinations of gases by exploiting the relative excitation probabilities of selected emission lines of the probe and ambient gases. The spectrual line technique taught herein is especially useful because it is nearly always possible to choose a characteristic spectral line for a gas which is relatively unambiguously distinguishable from the spectral lines of other residual and probe gases.

In another specific application of a dual partial pressure gauge, the apparatus of FIG. 11, in combinaton with a vacuum pump, samples the ambient air in the neighborhood of a liquid (alkali) metal heat exchange and cooling system such as may be found in a liquid metal cooled nuclear reactor. The contact of leaking alkali metal with air results in formation of hydrogen by chemical reaction with ambient water vapor. This may be monitored by utilizing the apparatus of FIG. 11 with one partial pressure channel responding to a selected hydrogen emission line and the second channel responsive to $N_2$. At a constant sampling rate the hydrogen signal will thus increase while the $N_2$ signal decreases and the ratio provides a sensitive indication of changes in hydroben concentration.

In another embodiment of the invention a periodic wave form can be applied to the excitation source by means well known in the art, thereby achieving corresponding intensity modulation of the emitted light and the ion current. The signal developed by the optical detector and the exciter current signal are constrained by processing synchronous with the periodic wave form in order to derive a response with enhanced signal to noise ratio and freedom from the effect of stray light.

Still another feature is the ability to protect the photomultiplifier from inordinately intense light emission. Such high intensities may be occasioned by high pressure or transient phenomena associated with fluctuations in the exciter. This protection is generally achieved by the derivation of the high voltage required for operation of the photomultiplier and the high voltage required for operation of the Penning cell exciter from a common source. Electrical isolation between photomultiplier high voltage and Penning cell high voltage is deliberately minimized in order that high currents drawn from the exciter cause the potential across the Penning cell to drop and thereby drop the high voltage supplied to the photomultiplier resulting in a corresponding decrease in the photomultiplier gain. The photomultiplier may thus be protected against high current drain which could permanently damage the tube.

In use as a partial pressure gauge or quantitative leak rate detector, the apparatus of FIG. 1 is first prepared by calibration operation. The reference for calibration for any arbitrary gas can be the 100% partial pressure point, that is the equation of partial pressure with total pressure achieved by introducing a quantity of the desired gas into the enclosure. For example, at a total pressure $10^{-6}$ torr the pressure is allowed to rise to $10^{-4}$ torr by introduction of the desired gas (both as read from switch setting C); the concentration of the desired gas is then at least 100 times that of other gases present and to an excellent approximation the fractional partial pressure output of FIG. 1 (as read from switch setting B) is calibrated at 100% of total pressure by adjusting the gain of photon detector 6 or amplifier 7. As will be understood by those skilled in the art, the total pressure output C for the particular exciter being used is pre-calibrated in conventional manner.

Another useful calibration point is available if the desired gas is present in a known concentration of some mixture of gases. One example is the relative composition of atmospheric air, the largest constituent (78%) of which is molecular nitrogen. If the gas within the vacuum enclosure is atmospheric air, the fractional partial pressure output of the apparatus of FIG. 1 is calibrated by observing the reading from switch setting B and if it is not 78%, then adjusting the gain as above until it does read 78%. Once the fractional partial pressure scale has been calibrated and the total pressure scale exists as pre-calibrated, the true partial pressure can be read on the same scale as the total pressure by using switch setting A instead of C. This gives a calibrated reading for partial pressure because the fraction of partial pressure to total pressure and the total pressure have both been calibrated. In other words, since two components of a three component relation are known, the third component is also known. If the pumping system which evacuates the vacuum enclosure is such as to effect disturbance of the relative fractional compositon of the gases therein (by preferential pumping speeds for different gases) the enclosure can be briefly isolated from the pump during the calibraton process.

Having established the total pressure scale, the fractional partial pressure scale and the partial pressure scale, it is apparent that the apparatus can operate as a total pressure gauge, a fractional partial pressure gauge and a partial pressure gauge. It should also be understood that use of the partial pressure or the fractional partial pressure output permits the apparatus to function as a leak indicator in situations where the presence of a leak would not be detectable from a total pressure measurement alone. In these situations a non-normal concentration distribution is indicative of a leak without systematic efforts to detect such leak. In other words, if the filter is selected for nitrogen, for example, and the fractional partial pressure varies from the system's normal non-leaking reading, the operator has an indication that a leak exists.

The nullling feature of the present apparatus is utilized in leak detecting to define a quiescent state, the departure from which state emphasizes the presence of a leak. In use, a bucking signal is applied at a convenient point in the system, for example, the input of the amplifier (7 in FIG. 1 and 115, 117 in FIG. 11) of an intermediate stage thereof, until a null is observed at the output. The gain is then increased until a significant departure from the previously adjusted null is evident, such departure arising from the error by which such bucking signal deviates from producing a true null. That is, the difference between the true null and the first approximation thereto becomes evident when the gain is increased. After a fine readjustment of the bucking signal, the null condition is restored and the process may be repeated until the desired gain is achieved. In this manner a very high gain may be achieved for observing small deviations from the quiescent state.

Although separate filters are shown in the detailed drawings, it should be understood that light dispersive elements such as a prism or grating (as in a monochromator) can be ued to sequentially detect each desired area of the total spectrum in situations where it is not necessary to obtain a simultaneous detection of plural partial pressures.

Since many changes can be made in the above construction and many apparently widely different embodiments of this invention could be made without departing from the scope thereof, it is intended that all matter contained in the above description and shown in the accompanying drawing shall be interpreted as illustrative and not in a limiting sense.

What is claimed is:

1. A vacuum pressure gauge comprising a tubular housing enclosing a Penning cell including a cathode and an anode, a window hermetically sealed to the side of said housing adjacent said cell, an opaque container attached to said housing and enclosing a photomultiplier, said container having a light filter therein aligned between said window and said photomultiplier, said container having a tubular portion connected to the side of said housing and containing said filter, said container having a second tubular portion substantially parallel to said tubular housing and containing said photomultiplier, first contact pins for said cathode and anode projecting through one end of said tubular housing, said photomultiplier having second contact pins projecting in the same direction as said first contact pins, and a unitary socket receiving said first and second pins.

2. A vacuum pressure gauge comprising a Penning cell including an anode and a cathode, a photomultiplier positioned to receive light from said Penning cell, magnet means for providing a magnetic field through said Penning cell, a magnetic yoke for said magnet means, said yoke being positioned between said Penning cell and said photomultiplier to provide a magnetic shielding for said photomultiplier, and said yoke having an aperture to permit light from said cell to reach said photomultiplier.

* * * * *